United States Patent

Parks-Root

(10) Patent No.: US 11,723,827 B1
(45) Date of Patent: Aug. 15, 2023

(54) BIODEGRADABLE BURIAL POD WITH DECOMPOSITION ELEMENT

(71) Applicant: Debra Parks-Root, Henderson, NV (US)

(72) Inventor: Debra Parks-Root, Henderson, NV (US)

( * ) Notice: Subject to any disclaimer, the term of this patent is extended or adjusted under 35 U.S.C. 154(b) by 306 days.

(21) Appl. No.: 17/209,190

(22) Filed: Mar. 22, 2021

Related U.S. Application Data

(60) Provisional application No. 62/964,315, filed on Jan. 22, 2020.

(51) Int. Cl.
*A61G 17/007* (2006.01)
*C12N 1/14* (2006.01)

(52) U.S. Cl.
CPC ....... *A61G 17/0136* (2017.05); *A61G 17/007* (2013.01); *C12N 1/14* (2013.01)

(58) Field of Classification Search
CPC .............. A61G 17/007; A61G 17/0136; A61G 17/047; A61G 2203/90; E04H 13/00; C12N 1/14
USPC .......................................................... 27/2, 7
See application file for complete search history.

(56) References Cited

U.S. PATENT DOCUMENTS

| | | | | |
|---|---|---|---|---|
| 3,918,133 A * | 11/1975 | Schmitz | ............. | A61G 17/0136 27/7 |
| 3,964,140 A * | 6/1976 | Gauchard | ............ | A61G 17/047 27/11 |
| 5,701,642 A * | 12/1997 | Order | ...................... | E04H 13/00 27/2 |
| 7,555,819 B2 * | 7/2009 | Wensley | ............ | A61G 17/0106 27/3 |
| 7,636,991 B1 * | 12/2009 | Scalisi, III | .............. | E04H 13/00 27/35 |
| 2002/0032954 A1 * | 3/2002 | Vazquez-Perez | ....... | E04H 13/00 27/1 |
| 2009/0241309 A1 * | 10/2009 | Smith | ................ | A61G 17/0136 27/2 |
| 2011/0000058 A1 * | 1/2011 | Spiers | .................. | A61G 17/047 27/1 |
| 2015/0067997 A1 * | 3/2015 | Biller | .................. | H04L 63/1441 27/13 |
| 2022/0015975 A1 * | 1/2022 | Hasnaoui | ............. | A61G 17/007 |
| 2023/0080744 A1 * | 3/2023 | Trammell | ............ | A61G 17/007 |

* cited by examiner

Primary Examiner — William L Miller
(74) Attorney, Agent, or Firm — Newman Law, LLC

(57) ABSTRACT

A biodegradable burial pod, comprising a shell and a lid defining a cavity therein, the shell and the lid being composed of a biodegradable resin, wherein an inner wall of one of the shell and the lid includes living mushroom spores disposed thereon, wherein one or more channels are defined in the inner wall thereof to receive fluids, the one or more channels having one or more outlets opening through the inner wall, the one or more channels being angled to facilitate flow of fluids to the one or more outlets, and wherein the lid includes a substance disposed thereon which is consumed by the mushroom spores.

1 Claim, 2 Drawing Sheets

BIODEGRADABLE BURIAL POD WITH DECOMPOSITION ELEMENT

BACKGROUND OF THE INVENTION

The embodiments of the invention generally relate to caskets and coffins for the burial of post mortem bodies.

Burial caskets or coffins evolved from a wooden box with a flat cover. A vast majority of the useable volume in today's burial caskets is still in the bottom part. Some areas, by tradition use a "half couch" casket with a two-part cover, which make any internal volume in the cover unusable. The covers are attached to the casket's bottoms with hinges.

If a cadaver is going to be viewed for a day or two, most funeral homes require it to be embalmed to slow down the deterioration and reduce the accompanying odor. This process replaces the normal bodily fluids with formaldehyde, a very dangerous and toxic chemical. The procedure is considered intrusive and tolerated only to permit one or two days of funeral home viewing.

Most of the caskets made in the United States are made of steel or wood. These materials in damp condition deteriorate. Many variables including the thickness of the material used, type of finish, amount of moisture present, chemicals present, galvanic conditions, etc., will actually determine how long before the structural integrity of the casket is compromised. Bodily and embalming fluids supply moisture and chemicals to the casket internally.

Other more corrosion-resistant metals are used such as copper/bronze and stainless steel, but sparingly because of the high cost. Even these metals deteriorate, especially when the conditions for galvanic corrosion are present. Some steel caskets use anodes to delay the galvanic corrosion. Fiberglass is used in some caskets. While it is resistant to corrosion, its relatively high cost makes it too expensive to make it thick enough to be structurally sound.

When caskets structurally collapse, the dirt above the casket caves in and the cemeteries had to fill in the hole with dirt. To alleviate this problem, many cemeteries now require concrete vaults. Decayed caskets and porous concrete vaults still could allow bodily and embalming fluids to contaminate the surrounding ground water. More expensive vaults with plastic and metal linings prevent this. If sometime in the future, cemeteries are dedicated to other uses, or more stringent environmental laws are passed, it will be costly to remove and dispose of or relocate these heavy concrete vaults and the caskets contained therein.

As it is well known, in the last 150 years there has been a significant increase in carbon dioxide (and harmful gases in general) emitted in the atmosphere (from about 280 ppm in 1850 to about 398 ppm in 2013), mainly due to human activities contemporary to and following the Industrial Revolution. As it is further known, and considering the constant level of carbon dioxide of natural origin, about 22% of the present carbon dioxide concentration in the atmosphere derives from human activities like the use of fossil fuels, deforestation due to cutting and/or burning, indiscriminate cementing and so on. The production of caskets undoubtedly is one of human activities contributing to above mentioned increase of carbon dioxide and harmful gases emissions in the atmosphere, of energy consumption and unavoidably also of deforestation.

SUMMARY OF THE INVENTION

The invention has many important advantages overcoming the deficiencies cited above, among other things, and provides a completely biodegradable and compostable burial pod which advances decomposition of its contents through the use of biopolymers and organisms such as fungi. The invention therefore reduces the emission of carbon dioxide and harmful gases into the atmosphere, as well as the energy consumption, waste and costs deriving from current burial practices.

Some embodiments of the invention are directed to a biodegradable burial pod, comprising a shell and a lid defining a cavity therein, the shell and the lid being composed of a biodegradable resin, wherein an inner wall and/or exterior wall of one of the shell and/or the lid includes living mushroom spores disposed thereon, wherein one or more channels are defined in the inner wall thereof to receive fluids, the one or more channels having one or more outlets opening through the inner wall, the one or more channels being angled to facilitate flow of fluids to the one or more outlets, and wherein the lid includes a substance disposed thereon which is consumed by the mushroom spores.

Other embodiments, features and advantages of the invention will be readily appreciated and apparent from the following detailed description when considered in connection with the accompanying drawings.

BRIEF DESCRIPTION OF THE DRAWINGS

Various advantages of the invention will be readily appreciated as the same becomes better understood by reference to the following detailed description when considered in connection with the accompanying drawings. The components in the figures are not necessarily to scale, emphasis instead being placed upon illustrating the principles of the invention.

DETAILED DESCRIPTION OF THE INVENTION

The invention is generally directed to a burial pod fabricated of material that is biodegradable and compostable while having characteristics of initial rigidity and strength, similar to properties of wood and which is preferably at least semi-permeable to oxygen.

Figure 1:
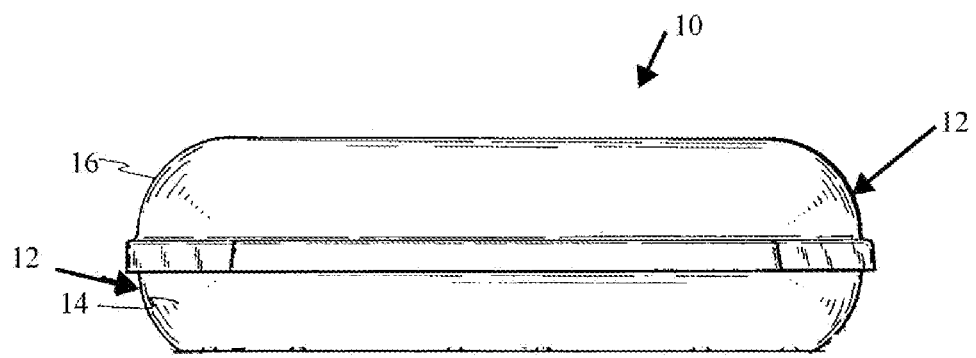
FIG. 1 illustrates an assembled burial pod of the invention.

FIG. 1 illustrates a burial pod of the invention generally referred to by the reference numeral 10. Pod 10 includes a body 12 comprising a container or shell 14 and cover or lid 16 defining a hollow cavity configured and dimensioned to be used as a burial chamber for receiving a cadaver therein. In this embodiment, shell 14 and lid 16 are concave and cooperate with one another to substantially define and enclose the hollow cavity within body 12. In some embodiments, burial pod 10 has a body 12 constructed of a polymer that is of renewable animal or vegetal origin. In some embodiments, body 12 is constructed of biodegradable layers made of polylactic acid, polyvinyl alcohol, starch, and combinations of these materials In some embodiments, a burial pod of the invention, such as burial pod 10 having shell 14 and lid 16, is modular in design, being formed of a material that can be created by a 3D printer. Although shell 14 and lid 16 are depicted as being concave, the body, including shell and lid, may be of any shape, with the shell generally defining at least a portion of a burial chamber therein. In some embodiments, the material is an organic polymer such as lignin. The use of 3D printing advantageously enables a burial pod of the invention to be created in the size desired upon demand.

In some embodiments, the burial pod shell and lid are configured to attach to one another without the need for adhesive. The burial pod of the invention may further include internal and external accessories formed of biopolymers of animal and/or vegetal origin, as well as decorative features also formed of biopolymers of animal and/or vegetal origin. The burial pod of the invention may further include additional cavities formed therein, such as on lower portions of shell 14, for, among other things, forming one or more reservoirs for collecting decomposition gases and fluids. In some embodiments, shell 14 includes one or more channels defined in the lower portion thereof for receiving and collecting decomposition fluids.

In some embodiments, the burial pod of the invention further includes a biomass, which may include plants, fungi and/or microorganisms, that aid in decomposition of a post mortem body inside the burial pod, neutralize toxins found in the body and/or transfer useful nutrients to plants that facilitate plant life. The biomass may be embedded or attached to the interior surfaces or wall of body 12.

Figure 2:
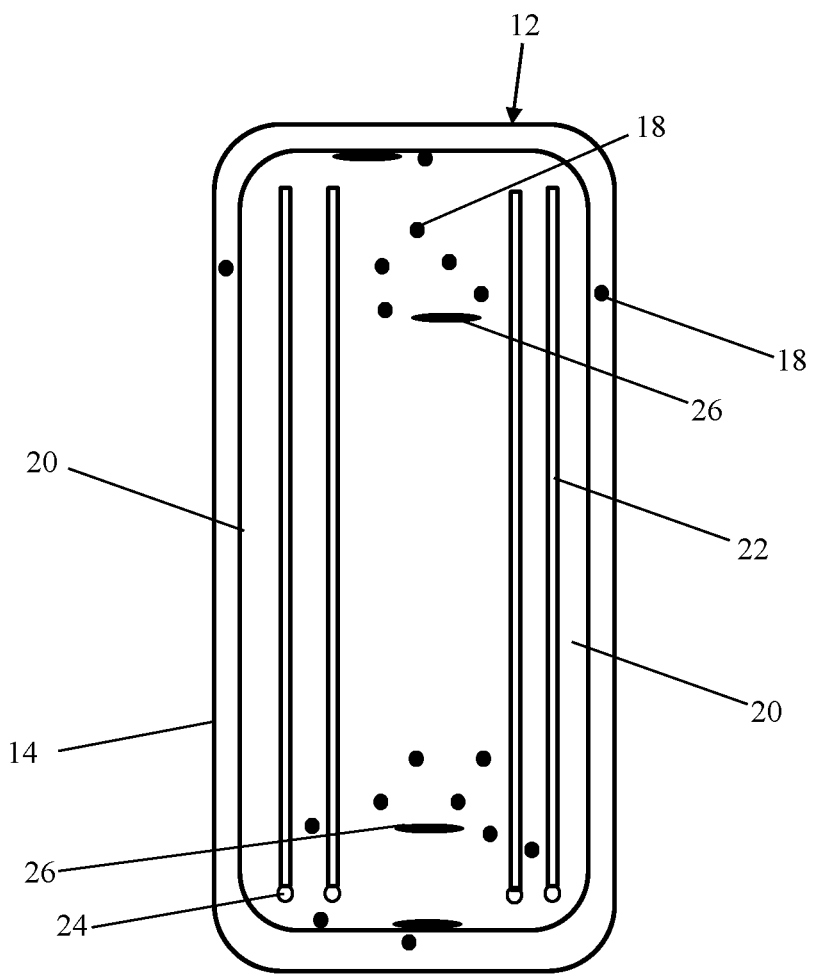
FIG. 2 illustrates a top view of the shell portion of the body of the burial pod of the invention.

As shown in FIG. 2, mushroom spores 18 are embedded and disposed on interior walls 20 of shell 14. Spores 18 may also be embedded and disposed on interior and/or exterior walls of shell 14 and/or lid 16 or other areas on the inner surfaces of the body 12, wherein the mushroom spores 18 aid in the decomposition of a post mortem body inside burial pod 10 and the overall biodegradability of burial pod 10. Channels 22 receive fluids and may include vents, drains or outlets 24 for release thereof. In some embodiments, channels 22 may be angled to facilitate the flow of fluids to outlets 24. A biomass 26 as described herein, which may also be used to decompose as well as provide a food source and be consumed by the mushroom spores 18 and other living bacterium or decomposers within body 12 of burial pod 10.

In some embodiments, the burial pod of the invention is constructed of a biodegradable resin, such as a synthetic resin, that completely decomposes into water, carbon dioxide, and methane gas within a few years by microorganisms, either in nature or disposed within the burial pod, such as bacteria or fungi. The decomposition of the biodegradable resin and body is caused by enzymes secreted by the microorganism. In some embodiments, any biodegradable resin composition containing polylactic acid as a main component may be used.

In some embodiments, mushrooms mycelium are added to shell 14 and/or lid 16, which break down post mortem remains by emitting enzymes to remove or eliminate toxins through mycoremediation. The biopolymer burial pod provides further nutrients and food for the fungi in addition to being biodegradable.

It should be understood that no limitation of the scope of the invention is intended by the examples provided. It should also be understood that the aforementioned embodiments of the invention may be of any size or shape. For example, the burial pod may be any burial container of bodies or remains, such as caskets or urns. Any alterations and further modifications of any inventive feature illustrated herein, and any additional applications of the principles of the invention as illustrated herein which would normally occur to one skilled in the relevant art and having possession of this disclosure are to be considered within the scope of the invention claimed.

While exemplary systems and methods, and applications of methods of the invention, have been described herein, it should also be understood that the foregoing is only illustrative of a few particular embodiments with exemplary and/or preferred features, as well as principles of the invention, and that various modifications can be made by those skilled in the art without departing from the scope and spirit of the invention. Therefore, the described embodiments should not be considered as limiting of the scope of the invention in any way. Accordingly, the invention embraces alternatives, modifications and variations which fall within the spirit and scope of the invention as set forth by the claims herein and equivalents thereto.

The invention claimed is:

1. A biodegradable burial pod, comprising a shell and a lid defining a cavity therein, the shell and the lid being composed of a biodegradable resin, wherein an inner wall of one of the shell and the lid includes living mushroom spores disposed thereon, wherein one or more channels are defined in the inner wall thereof to receive fluids, the one or more channels having one or more outlets opening through the inner wall, the one or more channels being angled to facilitate flow of fluids to the one or more outlets, and wherein the lid includes a substance disposed thereon which is consumed by the mushroom spores.

* * * * *